United States Patent [19]

Sendeff et al.

[11] Patent Number: 4,916,392

[45] Date of Patent: Apr. 10, 1990

[54] CONTACTLESS CURRENT CONTROL SENSOR IN APPARATUS FOR MAGNETOELECTRIC CRACK DETECTION

[75] Inventors: Eduard Sendeff, Aalen-Nesslau; Johannes Sebulke, Häusern, both of Fed. Rep. of Germany

[73] Assignee: Tiede GmbH & Co. Rissprufanlagen, Fed. Rep. of Germany

[21] Appl. No.: 97,191

[22] Filed: Sep. 16, 1987

[30] Foreign Application Priority Data

Sep. 17, 1986 [DE] Fed. Rep. of Germany ....... 3631571

[51] Int. Cl.⁴ ...................... G01N 27/87; G01R 33/12
[52] U.S. Cl. .................................. 324/235; 338/32 H; 324/263
[58] Field of Search .............. 324/209, 225, 226, 227, 324/228, 233, 234, 235, 263, 117 H; 338/32 H, 32 R

[56] References Cited

U.S. PATENT DOCUMENTS

| | | | |
|---|---|---|---|
| 3,359,995 | 12/1967 | McMaster et al. | 324/235 |
| 3,450,986 | 6/1969 | Chapman et al. | 324/235 |
| 3,694,740 | 9/1972 | Bergstrand | 324/235 X |
| 4,087,749 | 5/1978 | McCormack | 324/263 X |
| 4,409,585 | 10/1983 | Rousseau | 324/208 X |
| 4,482,865 | 11/1984 | George, Jr. | 324/263 |
| 4,539,520 | 9/1985 | McBride | 324/251 X |
| 4,665,361 | 5/1987 | Dorsch et al. | 324/263 X |

FOREIGN PATENT DOCUMENTS

| | | | |
|---|---|---|---|
| 630038 | 5/1936 | Fed. Rep. of Germany | 324/263 |
| 2827203 | 1/1980 | Fed. Rep. of Germany | 324/263 |
| 3130277 | 2/1983 | Fed. Rep. of Germany | . |
| 910496 | 11/1962 | United Kingdom | 324/263 |

OTHER PUBLICATIONS

Kaiser, L. U. A.: Strom und Positionssteuerungen mit Linearen Hallensensoren. In: Feinwerktechnick und Messtechnick 88, 1980 Nr 6, pp. 304–306.

Primary Examiner—Reinhard J. Eisenzopf
Assistant Examiner—Warren S. Edmonds
Attorney, Agent, or Firm—Steinberg & Raskin

[57] ABSTRACT

An apparatus is provided for measuring the test current in magnetoelectric fault detection, for instance by the magnetic particle method. A sensor comprising a Hall generator or a magnetoresistor is movably mounted on a diamagnetic support which clamps the sensor at a variable distance from a conductor carrying the test current. Alternatively, a plurality of sensors can be fixed to the support and the appropriate sensor selected for use.

7 Claims, 3 Drawing Sheets

CONTACTLESS CURRENT CONTROL SENSOR IN APPARATUS FOR MAGNETOELECTRIC CRACK DETECTION

BACKGROUND OF THE INVENTION

The invention relates to an apparatus for use in magnetoelectric crack detection, such as an apparatus comprising a sensor in the form of a Hall generator or magnetoresistor disposed in a retaining device and generating without contact a measuring quantity corresponding to the current in a test current conductor. The conductor may be a separate test conductor or may be the test-piece itself when appropriate. The apparatus may be used in the magnetic particle process for detecting cracks on the surfaces of work-pieces.

Magnetoelectric crack-detection is an important nondestructive test method. In the method, the test-pieces have to be magnetized so that the surface to be detected can be indicated by the resulting magnetic leakage flux. These magnetization processes are classified in DIN 54130. Except for magnetization by permanent magnets, which is economically unimportant. magnetization is always brought about by a predetermined current which generates a field in a coil which is then conveyed through the test piece, or alternatively the field-producing current is conveyed directly through the work-pieces (test-piece). The value of the current defines the value of the tangential field strength, which is critical in this process. This connection is particularly clear in the case of direct automatic flux (code letters SS in DIN 54130).

However, the current value is dependent not only on the characteristic of the qenerator but particularly on the total resistance of the the circuit. Particularly large inaccuracies are caused by fluctuations in contact resistance resulting from inaccurate coupling of the test-piece to the test circuit, or through scale or similar influences.

The current which actually flows, therefore, is one of the most important test preconditions for the entire process. If it is within the set tolerance range and can be kept constant, by a manual readjustment or by an electronic control system, the most important test precondition is fulfilled.

Owing to the importance of the correct current flow in magnetoelectric crack testing, it has long been the practice to measure the test current directly in high quality apparatus. The test current is characterized by high values (between 10 A and 20,000 A) and low voltages (below 42 V). It is known to measure these currents by using shunt resistors (DIN 43703) in the case of current generator for magnetoelectric crack testing. In shunt resistors the voltage drop in calibrated conductors is the quantity for measuring the current flowing. Shunt resistors are suitable for DC and AC but have the disadvantage that they cannot indicate rms values for the currents, which are mainly phase-controlled. This disadvantage is particularly serious in the case of phase-controlled AC and phase controlled half-wave DC, since DIN 54131 part 1 specifically describes the rms value as the control value for magnoelectric fault testing. Another disadvantage of shunt resistors is that a special size is needed for each current range. For example, about 35 sizes are needed for the range from 1 A to 15,000A. Each size is large and heavy. For example a shunt resistance for 10,000A measures about 185 $\times$ 206 $\times$ 170. Another disadvantage is the high price. As a result of these shunt resistors, the generators are large, heavy and expensive. Storage is also difficult and expensive, owing to the wide variety of parts. It becomes correspondingly difficult to supply spare parts on a worldwide scale.

It is also known to use current transformers to measure the test current in the case of magnetoelectric crack detection. In this case the high current is conveyed to a coil. The secondary current produced in the coil is proportional to the test current and therefore serves as a value for measuring. However, current transformers are suitable only for AC. The rms value of the current, which is required for detecting surface cracks, can be determined only approximately. using a moving-iron instrument. As before, each size is suitable only for a limited range of current, and there are over thirty sizes in the current range of 10A to 20,000A used for magnetoelectric crack detection. The space needed for current transformers is even greater than for shunt resistors, and the prices are likewise high. However, the most serious disadvantage both of current transformers and of shunt resistors is that neither system is universal but is suited for special kinds of currents. According to DIN 54130, however, all kinds of currents, e.g. DC, AC, half-wave DC and full-wave DC, are used depending on the purpose of the test, the shape of the test-piece and the required depth of penetration. Generators for magnetoelectric crack detection are therefore often constructed so that they can supply a number of kinds of current. For example an AC/DC generator can supply DC, AC and half-wave DC to DIN 54130. In order to determine the prescribed rms value of the phase-controlled current in this case, therefore, these devices must contain a DIN 43703 shunt resistor for DC and also a transformer and moving-iron instrument for AC.

It is known to use a Hall sensor or "Lohet" for vehicle ignition distributors or in sewing-machine needle control systems for controlling the travel or angle of rotation or amplitude of oscillation. Such devices serve as a current or magnetic barrier or for position control or the like, usually with an additional permanent magnet. Furthermore, in a particular power current system a Hall generator is rigidly incorporated in a resin in a pot-shaped magnet core of compacted powder, to give better external inductive screening to the sensor.

The details of these arrangements are closely related to a particular construction irrelevant to fault-detecting devices, or to general physical properties of the Hall sensor.

SUMMARY OF THE INVENTION

According to one aspect of the invention, there is provided an apparatus for use in maqnetoelectric crack detection, comprising : a sensor comprising one of a Hall generator and a magnetoresistor; and clamping means made of a diamagnetic material for clamping said sensor to a test current conductor at a variable distance therefrom.

According to another aspect of the invention, there is provided an apparatus including a guide track on said clamping means movably mounting said sensor to said clamping means.

It is thus possible to provide an apparatus which can be used for all required kinds of currents and through the entire range of currents occurring in magnetoelectric crack detection, and which is rugged, does not break down easily, and can easily be adapted to particular test conditions.

In the case of fault-testing, such apparatus, is in principle suitable for full or half-wave DC, DC and phase-controlled DC, owing to the adjustability of a magneto-resistor or the Hall generator which is known in physics. The retaining device covers the entire range of test current required for magnetoelectric fault detection and saves the need for a number of measuring shunt resistor; Also a single test and retaining device can be rapidly adapted and accurately adjusted to a new test problem, a new series of work-pieces or the like, owing to the simplified construction and arrangement. The test device is equally useful for portable apparatus, small apparatus, large stationary apparatus and the like. Complicated calibration processes over the entire measuring range are replaced by normal processes for calibrating the full scale values. Another advantage is that the rms value of the test current can be obtained in simple manner from the sensor signals. Using a downstream-connected electronic circuit. This is irrespective of the nature and frequency of the test current. The sensor can be incorporated inside a control circuit of a highly accurate constant current regulating system. This sensor arrangement also saves costs.

The following relations apply to a Hall generator in such an apparatus.

The measured voltage $U_H$ taken from the generator is:

$$U_H = \frac{R_H}{d} \cdot I_{st} \cdot B$$

In this equation, $U_H$ is the measuring voltage for (the Hall voltage) originating at the Hall generator, are $R_H$ is the resistance of the Hall generator (the Hall constant of the generator material), d is the thickness of the Hall element. $I_{st}$ is the control current passing through the Hall element, and B is the magnetic flux density (induction), which results from the actual test current conductor and acts on the Hall generator.

The Hall generator must be operated in air or in plastics, i.e. at places where the relative permeability $\mu$ is unchanged (diamagnetic substances)

$\mu = \mu_o$ =constant =B/H ; B =H $\mu_o$ =const. ×H
where H is the field strength penetrating the Hall generator. The control current, $I_{st}$ is kept constant, so that;

$U_H \sim H$.

The voltage across the contacts of the Hall generator is therefore proportional only to the field strength penetrating the Hall element.

As a further consequence, the field strength produced in the neighborhood of a straight conductor carrying the test current conforms to the physical relation :

$$H = \frac{I_{pr}}{2\pi r}$$

where H is the induced field strength, $I_{pr}$ is the test current in the conductor and r is the distance of the measuring-point from the center of the conductor. Consequently the Hall generator generates a voltage $$U_H = \frac{R_H}{d} \cdot I_{st} \cdot \mu_o \cdot \frac{1}{2\pi} \cdot \frac{I_{pr}}{r} ;$$

where d, $I_{st}$ and $\mu_o$ are kept constant and R is a constant (the Hall constant).

If the product of the constant terms is represented by C, :

$$U_H = C \cdot \frac{1}{r} \cdot I_{pr}$$

Accordingly a voltage directly proportional to the required test current $I_{pr}$ can be taken from the sensor.

If the center point of the test current conductor is suitable adjusted, a single sensor and clamping device can be used for testing small or large currents as required. Consequently a single clamping means and sensor are sufficient for the entire current range required for magnetoelectric crack detection, e.g. from 10A to 20,000A.

An electronic system may be used which, in all cases, irrespective of the nature of the current, uses the signals of the sensor to calculate the rms value required in each case of magnetoelectric crack detection.

The sensor can also advantageously be used in a control circuit of a known constant-current regulating system. Independently of the nature of the current, therefore, the selected test current can be reliably kept constant within the power range of the apparatus. The current sensor can now be used as the basis of a downstream electronic system by means of which certain functions or displays important for magnetoelectric crack testing, e.g. demagnetization function, pulse magnetization and digital indication, are brought about more accurately than hitherto.

BRIEF DESCRIPTION OF THE DRAWINGS

An embodiment of the invention is shown in the drawings and will be described hereinafter in detail. In the drawings.

DESCRIPTION OF THE PREFERRED EMBODIMENTS

Figure 1:
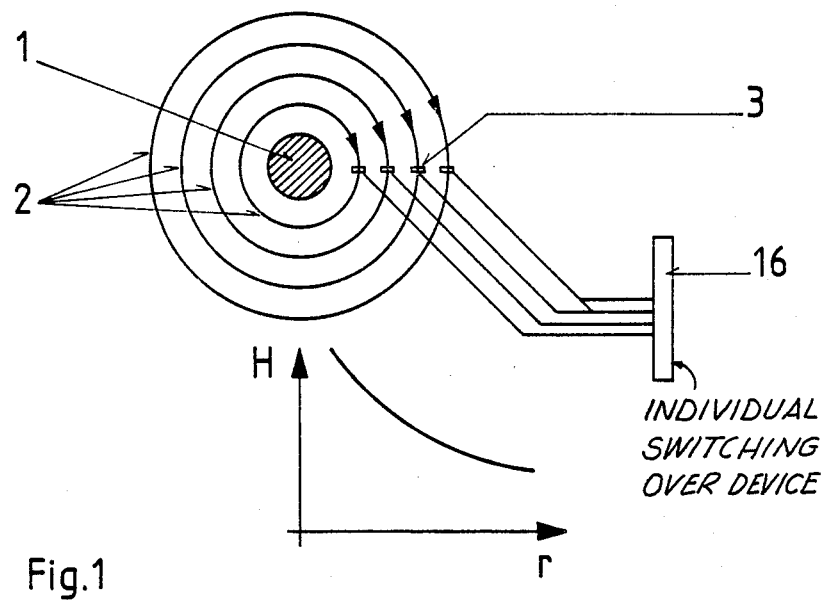
FIG. 1 is an end view of a test current conductor shown in section, schematically indicating the magnetic lines of flux and the arrangement of the Hall generator at four different places.
Figure 2:
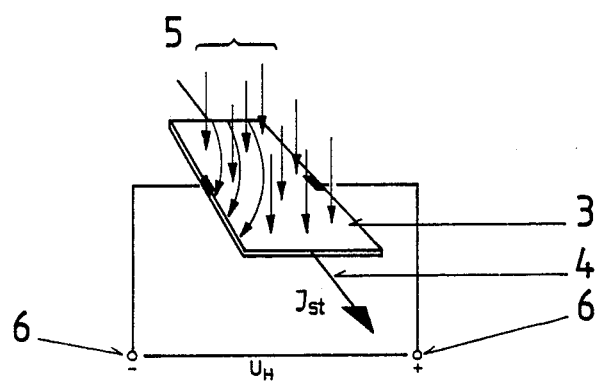
FIG. 2 is a perspective view of a Hall conductor and associated metal contact for the Hall volta $U_H$ showing the direction of the associated control current $I_{st}$.

FIG. 1 diagrammatically shows a Hall generator (3) at various radial distances from a test current conductor (1) and the magnetic lines of flux (2) produced by the conductor (1), under which the magnetic field strength (H) is shown along the ordinate in dependence on the radial distance (r). Depending on the absolute value of the current to be measured in conductor (1). the Hall generator (3) is disposed at a varying radial distance, to the left and close to the conductor (1) in the case of a small test current and at the outside right in FIG. 1 in the case of a large test current. In this manner the same Hall generator always gives the same high percentage accuracy. FIG. 2 shows at 4 the control current $I_{st}$ flowing through the plate-shaped Hall generator (3) the magnetic flux density (5) penetrating it, and the Hall voltage $U_H$ generated by the Hall generator (3) and used as the quantity to be measured.

Figure 3:
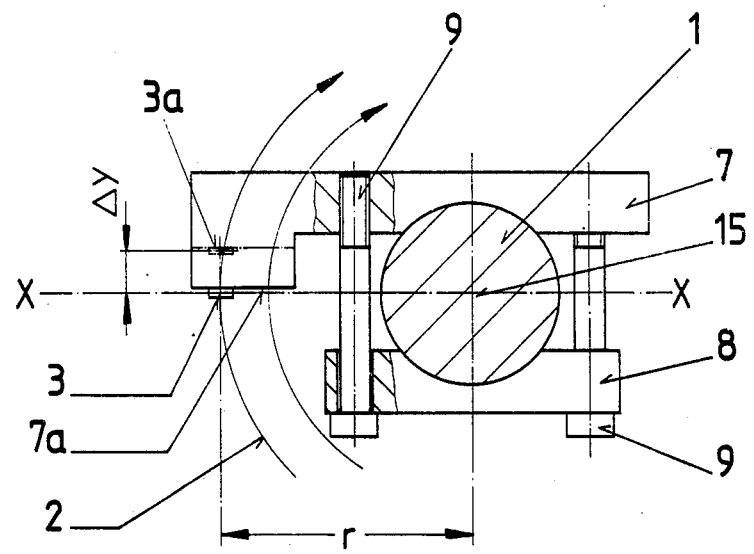
FIG. 3 is an end view of the test current conductor showing its position relative to the retaining device and Hall generator.
Figure 4:
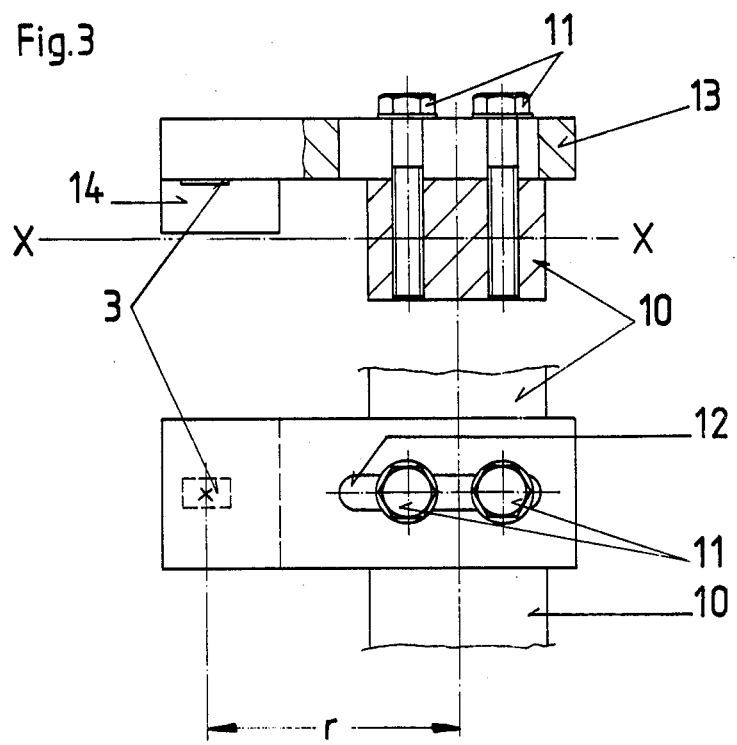
FIG. 4 is a front view and associated plan view of a rectangular test current conductor directly provided with securing bolts for the device for retaining a Hall generator which is embedded or screened by a cover component, a part of the retaining device being optionally adjustable together with the Hall generator relative to the test current conductor.

FIGS. 3 and 4 show advantageous embodiments. The magnetic lines of flux (2) induced by the test current of conductor (1) are shown only partially. A retaining device comprises a top part (7) and a bottom part (8), advantageously in the form of a clamping device, held together by bolts (9). The Hall generator (3) is disposed in the optimum axis X-X. Depending on circumstances, e.g. for reasons of space, the Hall generator can be moved by an amount 6y relative to the axis x-x, as is shown by broken lines. As the drawing shows, the Hall generator (3) is disclosed at a set distance r from the center point (15) of the conductor. However, the distance is adjustable, depending on whether the Hall generator is used as a sensor for a large or small test current, as already explained with reference to FIG. 1. Various advantageous embodiments are possible for this purpose. The Hall generator (3) can be disposed on the top part (7) at a greater or lesser distance from the center (15) as required, and can be stuck to a center surface (7a) of the clamping device which is provided, e.g. with an adhesive layer. In a variant (compare FIG. 1) a number of Hall generators are permanently stuck at various distances (i) from the center (15) of the conductor (1) and only the appropriate Hall generator has its $U_H$ outPut terminals (6) (compare FIG. 2) connected to the measuring or control circuit, which advantageously has an individual switching-over device (16), which can advantageously contain a shift register for increasing the time and space range of measurement.

Figure 5:
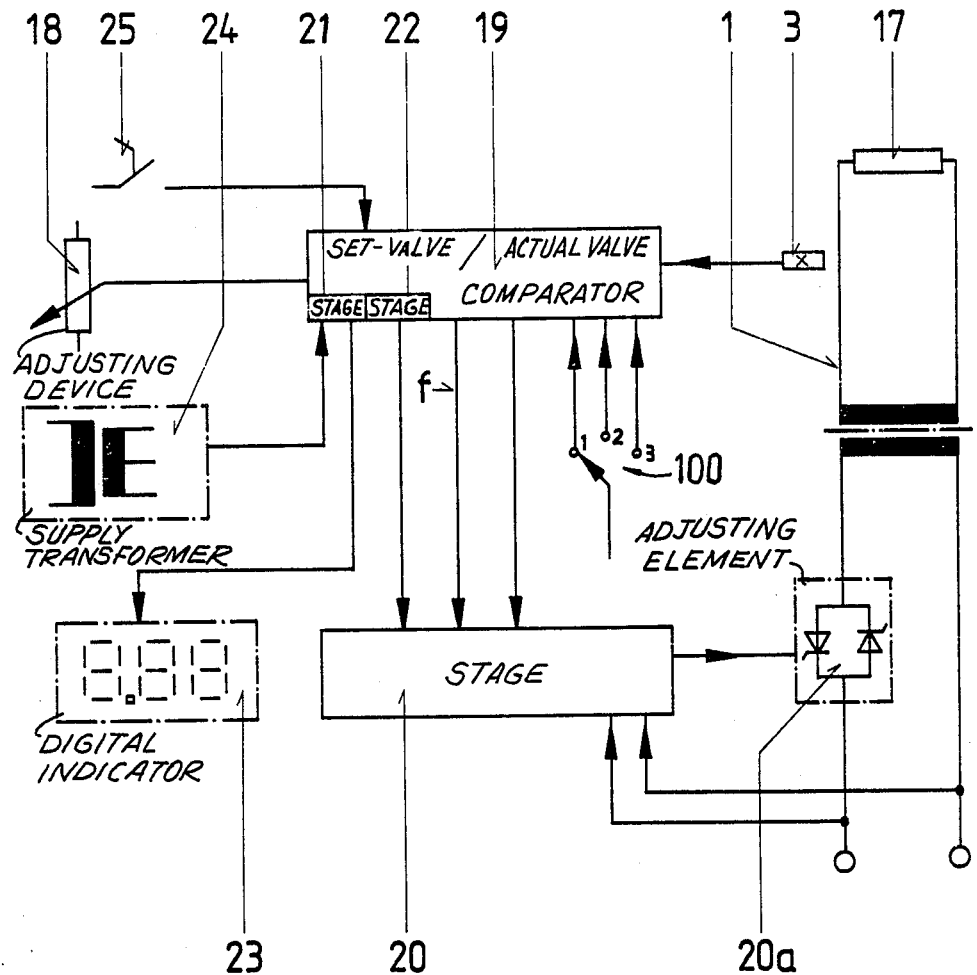
FIG. 5 is a diagram, partly in block form, of a control circuit for the circuit containing the test current conductor.

Alternatively the Hall generator or generators or their associated bearing plates can be adjustably, e.g. slideably, Mounted in a guide track, e.q. a guide rail or groove, on the retaininq device (7, 8; 13, 9). In that case the guide track advantageously extends radially in the direction of the center (15) of the test current conductor (1). For constructional reasons the Hall generator can advantageously be adjusted or slid concentrically relative to the center (15) or the periphery of the conductor (1), as shown by the displacement of the Hall generator (3, 3a) in FIG. 3. The guide tracks may also be combined. A simple, reliable and economic embodiment thereof is shown in FIG. 4, where a test circuit conductor (10) is given a rectangular cross-section. The clamping means in FIG. 3 is replaced in FIG. 4 by threaded bolts (11) which can be screwed directly to the test current conductor (10), or my extend through the conductor (1). A retaining plate (13) has a slot (12) through which the shafts of the bolts extend. The slot extends perpendicular to the axis of the conductor (1). The Hall generator (3) is therefore adjustable radially with respect to conductor (1), by loosening the bolts (11) and adjusting the retaining plate (13) and Hall generator to the desired distance r from conductor (1). after which the screws (11) are tightened. Advantageously the Hall generator (3) is displaced radially in line with the slot 12 (compare FIG. 4). If required, however, the slot may be displaced at an angle to the axis of conductor (1), for reasons of space or depending on individual components. The Hall generator 3 can be embedded in the retaining device, (7, 8, 13, 9) more particularly by being cast in or surrounded with plastics (compare FIG. 4). Alternatively the Hall generator (3) can be protected from mechanical damage in a simple rugged manner by a cover component, e.g. a part (14) of the retaining device stuck underneath. The Hall generator or generators (3, 3a) can be the sensor of an ordinary analog or digital measuring device in which the operator makes single or repeated reading or observation of a test current value proportional to the value $U_H$. Advantageously, however (FIG. 5) the associated circuit is provided with an electronic control circuit, since the test piece (17) can have any desired contact or volume resistance during magnetoelectric crack detection. In the present case, use is made of an adjusting device (18), e.g. a variable resistor, by means of which the test current (set value of current) can be preselected as required for the test. The test current is supplied to an electronic set-value/actual-value comparator (19) in which the actual value of the current supplied by the Hall generator (3) is compared with the set value. The result is used to calculate a command variable (f) which is stored in a stage (20) containing an electronic adjusting system for controlling an adjusting element (20a) in the primary circuit of a mains transformer, to adjust its primary current, resulting in a corresponding adjustment of the test current in the secondary circuit to the value required for testing the particular test-piece (17). The Hall generator (3) is therefore an electronic component of the complete control circuit shown in FIG. 5. Advantageously the electronic control system also comPrises by an electronic stage (21) connected by an associated line to an electronic stage (23) comprising a digital indicator. Advantageously also, operating functions frequently required in magnetoelectric crack detection can be incorporated in the circuit, e.g. in an electronic stage (22) which oPerates in dependence on preset current delay functions or pulse current magnetization and whose output is connected by an associated line to a corresponding input of the electronic adjusting stage 20, by means of which a corresponding setting element 20a correspondingly adjusts the magnetization current to an associated test piece 17, thus providing it with a control circuit. FIG. 5 also shows a switch component 25 for grounding the current and a component 24 serving as a supply transformer. The control software and hardware is of universal use, i.e. for both large and small currents with the same percentage accuracy and for portable, movable and stationary crack detectors, demagnetization devices and the like. A three-way switch 100 having inputs 1, 2, 3 is set in accordance with the desired mode of operation, e.g., input 1 corresponds to the magnetizing mode described above. Inputs 2 and 3 may correspond to demagnetizing and pulse modes as will be understood. It can also be used for all current linkage circuits in single or multiple circuit devices for all kinds of currents to DIN 54130 thus eliminating the variety of components and large number of shunt resistors. Magnetoresistors are thin plates of semi-conductor material, more particularly Indium Antimonide, the resistance of which changes when acted upon by a magnetic field. In an embodiment in the form of grid plate, the Hall voltage short-circuiting components are metal needles or strips disposed transversely to current $I_{st}$ and forming the individual resistance zones, thus producing a resistance plate. A second embodiment is a longitudinal or transverse field probe made from an InSb/NiSb eutectic with fine NiSb needles.

We claim:

1. A contactless test current control device in an apparatus for magnetoelectric crack detection,
   having a sensor comprising one of a Hall generator and a magnetoresistor and connected to clamping and retaining means made of a diamagnetic material for adjustably clamping said sensor with respect to a test current conductor at variable distances therefrom; said clamping and retaining means comprising a retaining plate and a guide track defining a slot extending substantially perpendicularly to the test current conductor;
   said sensor being mounted upon said retaining plate which is movable along said slot;
   further comprising a control circuit having an input connected to said sensor and an output for providing a test current control signal, and test current control means having an input connected to said output of said control circuit for controlling test current through the test current conductor,
   whereby magnetic field generated by the current passing through the test current conductor is sensed by said sensor without contacting the test current conductor.

2. A contactless test current control device in an apparatus for magnetoelectric crack detection,
   having a sensor comprising one of a Hall generator and a magnetoresistor and connected to clamping and retaining means made of a diamagnetic material for adjustably clamping said sensor with respect to a test current conductor having a circular cross-section at variable distances therefrom on a guide track on said clamping and retaining means that extends substantially radially to the test current conductor,
   said sensor movably mounted along said track of said clamping and retaining means,
   further comprising a control circuit having an input connected to said sensor and an output for providing a test current control signal, and test current control means having an input connected to said output of said control circuit for controlling test current through the test current conductor,
   whereby magnetic field generated by the current passing through the test current conductor is sensed by said sensor without contacting the test current conductor.

3. A contactless test current control device in an apparatus for magnetoelectric crack detection,
   having a sensor comprising one of a Hall generator and a magnetoresistor and connected to clamping and retaining means made of a diamagnetic material for adjustably clamping said sensor with respect to a test current conductor having circular cross-section at variable distances therefrom on a guide track on said clamping and retaining means that extends substantially tangentially with respect to the test current conductor,
   said sensor movably mounted along said track of said clamping and retaining means,
   further comprising a control circuit having an input connected to said sensor and an output for providing a test current control signal, and test current control means having an input connected to said output of said control circuit for controlling test current through the test current conductor,
   whereby magnetic field generated by the current passing through the test current conductor is sensed by said sensor without contacting the test current conductor.

4. A contactless test current control device in an apparatus for magnetoelectric crack detection,
   having a sensor comprising one of a Hall generator and a magnetoresistor and connected to clamping and retaining means made of a diamagnetic material for adjustably clamping said sensor with respect to a test current conductor at variable distances therefrom on a guide track on said clamping and retaining means, said clamping and retaining means including securing means for securing said clamping an retaining means directly to said test current conductor,
   said sensor movably mounted along said track of said clamping and retaining means,
   further comprising a control circuit having an input connected to said sensor and an output for providing a test current control signal, and test current control means having an input connected to said output of said control circuit for controlling test current through the test current conductor,
   whereby magnetic field generated by the current passing through the test current conductor is sensed by said sensor without contacting the test current conductor.

5. Apparatus according to claim 4, having a test current conductor of rectangular cross-sectional, in which said securing means comprise threaded bolts screwed to said conductor.

6. A contactless test current control device in an apparatus for magnetoelectric crack detection,
   having a sensor comprising one of a Hall generator and a magnetroresistor and connected to clamping and retaining means made of a diamagnetic material for adjustably clamping said sensor with respect to a test current conductor having a rectangular cross-section at variable distances therefrom on a guide track on said clamping and retaining means extending long surface of the test conductor,
   said sensor movably mounted along said track of said clamping and retaining means,
   further comprising a control circuit having an input connected to said sensor and an output for providing a test current control signal, and test current control means having an input connected to said output of said control circuit for controlling test current through the test current conductor,
   whereby magnetic field generated by the current passing through the test conductor is sensed by said sensor without contacting the test current conductor.

7. A contactless test current control device in an apparatus for magnetoelectric crack detection,
   having a sensor comprising one of a Hall generator and a magnetoresistor and connected to clamping and retaining means made of a diamagnetic material for adjustably clamping said sensor with respect to a test current conductor at variable distances therefrom on a guide track on said clamping and retaining means,
   said clamping and retaining means comprising a top part, a bottom part, and bolts for retaining said top and bottom parts together, said guide track comprising a slot or groove formed on one of said top and bottom parts, said sensor being movably mounted upon one of said top and bottom parts in said slot or groove formed therein comprising said guide track, further comprising a control circuit having an input connected to said sensor and an output for providing a test current control signal, and text current control means having an input connected to said output of said control circuit for controlling test current through the test current conductor, whereby magnetic field generated by the current passing through the test current conductor is sensed by said sensor without contacting the test current conductor.

* * * * *